United States Patent [19]
Kwak et al.

[11] Patent Number: 5,910,307
[45] Date of Patent: Jun. 8, 1999

[54] PROCESS OF EXTRACTING AND PURIFYING BIOLOGICALLY EFFECTIVE INGREDIENTS FROM COMBINED MEDICINAL PLANTS AND THEIR EXTRACT COMPOSITION

[75] Inventors: Wie-jong Kwak; Chang-kyun Han, both of Seoul; Hwan-su Kim, Kyungki-do; Jae-suk An, Kyungki-do; Taek-soo Kim, Kyungki-do, all of Rep. of Korea

[73] Assignee: Sunkyong Industries, Ltd., Kyungki-do, Rep. of Korea

[21] Appl. No.: 08/716,058

[22] Filed: Sep. 19, 1996

[51] Int. Cl.$^6$ ............................. A01N 65/00; A61K 35/78
[52] U.S. Cl. ............................................. 424/195.1; 514/1
[58] Field of Search ............................... 424/195.1; 514/1

[56] References Cited

PUBLICATIONS

Research Archives of Useful Plants Resources in Korea, Korea Research Institute of Chemical Technology, pp. 780–781 (1988). (with English translation of relevant parts).
An Explanatory Diagram of Korean Medicinal Plants, Youn-grim Pub., pp. 489–490 (1990). (with English translation of relevant parts).
Research Archives of Useful Plants Resouces in Korea, Korea Research Institute of Chemical Technology, pp. 354–357 (1988). (with English translation of relevant parts).
An Explanatory Diagram of Korean Medicinal Plants, Youn-grim Pub., pp. 960–963 (1990). (with English translation of relevant parts).
Research Archives of Useful Plants Resouces in Korea, Korea Research Institute of Chemical Technology, pp. 480–482 (1988). (with English translation of relevant parts).
Chemical Research for Prunella Herba, Lee Jak–pyung et al., Bulletin of Medical College in Beijing, 17 (4), pp. 297–299 (1985). (with English translation of relevant parts).
Dong–Eui–Bo–gam, Hyangyak Gibsung–bang and Kwangjee Beakub (3 excerpts from conventional herbal books). (with English translation of relevant parts).
Journal of Pharm. Phamacol., 44 (5), pp. 456–458 (1992).
Chung–Kuo–Li–Hsueh–Pao, 10 (4), pp. 381–384 (1989). (with English Abstract).
Biochem. Pharmac., 29, pp. 533–538 (1980).
Agents Actions, 17, pp. 375–376 (1985).

*Primary Examiner*—Leon B. Lankford, Jr.
*Attorney, Agent, or Firm*—Christie, Parker & Hale, LLP

[57] ABSTRACT

This invention to a process of extracting and purifying biologically effective ingredients from combined medicinal plants and their plant extract composition and more particularly, to a process for effective extracting and purifying the biologically effective ingredients by mixing Clematis Radix, Trichosanthes root and Prunella Herba in a certain ratio, being useful for alleviating acute/chronic inflammation and also for inhibiting platelet/whole blood aggregation, abnormally proliferated immunocytes (e.g., B-lymphocyte, T-lymphocyte), inflammation-inducing enzymes (5-Lipoxygenase, Cyclooxygenase-I, Cyclooxygenase-II) and also scavenging activity on toxic active oxygen species when compared to a single plant extracts, together with their extract composition, which may be effectively used as an anti-inflammatory agent with analgesic effects, rheumatoid arthritis drug and agents for improving peripheral blood circulation.

13 Claims, 10 Drawing Sheets

PROCESS OF EXTRACTING AND PURIFYING BIOLOGICALLY EFFECTIVE INGREDIENTS FROM COMBINED MEDICINAL PLANTS AND THEIR EXTRACT COMPOSITION

BACKGROUND OF THE INVENTION

1. Field of the Invention

This invention relates to a process for extracting and purifying the biologically active ingredients from combined medicinal plants, and to their plant extract composition. More particularly, this relates to a process for effective extracting and purifying the biologically effective ingredients from mixed Clematis Radix, Trichosanthes root and Prunella Herba in a certain ratio. These extracts are useful for alleviating the acute/chronic inflammation for inhibiting platelet/whole blood aggregation, immunocytes proliferation (e.g., B-lymphocyte, T-lymphocyte), inflammation-inducing enzymes (5-Lipoxygenase, Cyclooxygenase-I, Cyclooxygenase-II) and scavenging activity of superoxide radicals when compared to each single plant extract. This invention also includes their extract composition, which may be effectively used as an anti-inflammatory agent with analgesic effects, rheumatoid arthritis drug and blood agent for improving peripheral blood circulation.

2. Description of the Prior Arts

Clematis Radix, Trichosanthes root and Prunella Herba are well known as medicinal plants. Each medicinal plant has long been used in the form of aqueous plant extract and its powder. Such plants have been widely used for the treatment of general inflammations such as skin rashes or wounds, bronchitis, mastitis, peritonsillitis and anal fistula, and also for the relief of cooled or numbed hands and feet, painful knees, painful waist and shoulder, fragile body and pain in the skin. These symptoms are similar to chronic rheumatoid arthritis in terms of the modern pathological concept.

Clematis Radix is a root of same genus in plant taxonomy, which is distributed in the shady forest throughout Korea. After removing cormophyte and root hair collected in autumn, Clematis Radix is finely chopped and dried in the sun for medicinal use. Clematis Radix, a non-toxic medicinal plant, has long been used for the treatment of the following symptoms such as pains in the extremities, decreased mobility in knee joints and paralysis in the extremities. In particular, clematis has been frequently used as a miraculous drug in those patients who feel uncomfortable while standing due to the coldness in waist, knee and feet. It is well known that clematis Radix including the same genus in plant taxonomy have various constituents, such as flavanone glycosides (e.g., clematin, etc.), saponins (e.g., clemontanoside A, clemontanoside B, clemontanoside C, clematoside S). Moreover, this plant is also found to contain glucoses and sterols [1. Research Archives of Useful Plants Resources in Korea, Korea Research Institute of Chemical Technology, pp780–781(1988), 2. An Explanatory Diagram of Korean Medicinal plants, Youngrim Pub., pp489–490 (1990)].

Trichosanthes root known as "multifarious medicines" or "Karokon" classified as a perennial creeping plant, is collected in autumn. The outer shells of cleanly washed roots are removed and the rest of the roots are cut appropriately and dried in the sun for medicinal use.

Trichosanthes root, a non-toxic medicinal plant, has been widely used for excretion of pus, vanishing the boil, detoxification and antipyretic effects, and also effective for thirst, various swelling, anal fistula and mastitis. It has been investigated up to now that Trichosanthes root contains trichosanthin as proteins, arginine and citrulline as amino acids, and palmitic acid and linoleic acid as fatty acids. Recently, Trichosanthes root is found to contain bryonolic acid, cucurbitacin B and α-spinasterol as sterols [1. Research Archives of Useful Plants Resources in Korea, Korea Research Institute of Chemical Technology, pp 354–357 (1988), 2. An Explanatory Diagram of Korean Medicinal Plants, Youngrim Pub., pp960–963(1990)].

Prunella Herba is a flower of prunella and same genus in plant toxonomy. When the flower of Prunella Herba is half withered during summer, the flower should be collected and dried in the sun for medicinal use. Prunella Herba, a non-toxic medicinal plant, has been used for the treatment of the following symtptoms such as chronic swelling, smallpox, acute mastitis and lymphocytic tuberculosis. Prunella Herba is also effective in destructing lumps (generated in a lower stomach owing to extravascated blood) or others, while treating beriberi and numbness in the extremities. It has been reported that Prunella Herba contains saponins such as oleanolic acid and ursolic acid, etc, and also contains carotene, vitamin C, vitamin K, tannin, caffeic acid and chlorogenic acid. Rosmarinic acid is also found in Prunella Herba [1. Research Archives of Useful Plant Resources in Korea, Korea Research institute of Chemical Technology, pp 480–482(1988) 2. Chemical Research for Prunella Herba, Lee Jak-pyung et al., Bulletin of Medical College in Beijing, 17(4), pp297–299(1985)].

The conventional herbal books (e.g., Dong-Eui-Bo-gam, Hyangyak Gibsung-bang and Kwangjee Beakub) or related literatures refer to the medical efficacy of herbs and processes of manufacture of aqueous herbal solution. But they only described a single prescription of each of these medicinal plants but not a formulation available for the manufacture of aqueous herbal solution from the combined preparation of medicinal plants. Furthermore, these medicinal plants were prepared by hot water extraction method. But any substances extracted by above method, showed no acquisition of detailed knowledge on biologically active ingredients.

SUMMARY OF THE INVENTION

In view of these situations, the present inventors have made an extensive research designed to scientifically utilize the combined preparation of Clematis Radix, Trichosabthes root and Prunellae Herba. Each of these plants are reported to have analgesic, anti-inflammatory effects and also to improve various symptoms (traditionally termed Bi-zheng) and to maximize the extract efficiency of active ingredients. Now, the present invention has been completed through the development of pharmacologically effective plant extract composition after extracting some active ingredients from the combined plants in a proper ratio with high yields.

The object of this invention is to provide a extraction process and medicinal plant extracts from mixed Clematis Radix, Trichosabthes root and Prunellae Herba in a proper ratio. This extract has biological effects and shows significant pharmacological activities, such as analgesic & anti-inflammatory effects, anti-coagulant actions in platelet and whole blood, inhibitory actions on enzymes associated with degradation of joint tissue, inflammation-inducing enzyme activity and regulation of abnormally proliferated immunocytes and also to improve scavenging actions on toxic active oxygen species, curation, scavenging actions on toxic active oxygen species and curation of chronic rheumatoid arthritis.

This invention is characterized by a combined plant extract composition containing Clematis Radix, Trichosabthes root and Prunella Herba.

A process for manufacturing the combined herbal preparations extracted with water or alcoholic solution is comprised of the following sequential steps:

(1) Clematis Radix, Trichosabthes root and Prunella Herba are mixed in a weight ratio of 1:0.5–2:0.5–1.5 and the mixture is partitioned with water or alcoholic solution; (2) The extracted solution is partitioned with an amount of water saturated n-butanol or propyl alcohol and then the alcohol layer is concentrated under reduced pressure; and (3) The concentrated extract is further concentrated with water by constant boiling and lyophilized to give an extract in powder form.

This invention is described in more detail as set forth hereunder.

This invention is characterized by combined plant extract composition containing Clematis Radix, Trichosabthes root and Prunellae Herba in a weight ratio of 1:0.5–2:0.5–1.5.

According to this invention, a combined plant extract composition would be obtained from the following steps, wherein;

1) Three kinds of medicinal plants containing Clematis Radix, Trichosabthes root and Prunella Herba are mixed in a weight ratio of 1:0.5–2:0.5–1.5. The resulting mixture is re-extracted with 10–15 volumes of water or alcoholic solution, extracted under reflux and filtered. Then, the residue is re-extracted with 7–12 volumes of water or alcoholic solution to the weight of said combined medicinal plants, heated and filtered. The filtrate is brought up with previously prepared solution and filtered.

2) The remaining solution obtained from the first step is removed alcoholics and then partitioned with a same amount of n-butanol saturated with water. The alcohol layer is concentrated under reduced pressure at 60–70° C.

3) By constant boiling two or three times, the residue is concentrated with 50–100 volumes of water to the total extract weight obtained from the second step, homogeneously suspended with a same amount of water and lyophilized to give a powdered extract. The combined plant extract composition of this invention, so formed, includes 0.3–0.6% (w/w) of rosmarinic acid and 3.0–7.0% (w/w) of oleanolic acid.

Furthermore, this invention includes some methods designed to use the combined plant extract composition as analgesic & anti-inflammatory agents, drugs for chronic rheumatoid arthritis and blood circulation enhancers.

As such, this invention relates to a process for extracting and purifying biologically active ingredients from three kinds of medicinal plants having remarkable analgesic & anti-inflammatory effects and also being effective for the treatment of chronic rheumatoid arthritis and blood circulation disorders. Among the three kinds of medicinal plants of this invention, Clematis Radix and Trichosabthes root collected in autumn are used, while Prunella Herba is collected in late summer.

Instead of the conventional methods that use each medicinal plant as a single preparation, three kinds of medicinal plants collected during such different periods are mixed in a proper ratio and extracted so as to prepare a combined preparation in a proper ratio. Clematis Radix, Trichosabthes root and Prunella Herba are mixed in a weight ratio of 1:0.5–2:0.5–1.5. If the blending ratio of said medicinal plants is not in the above range, the composition of active ingredients (e.g. rosmarinic acid, oleanolic acid) will not be proper. So, reduced or excessed constituents, having analgesic & anti-inflammatory actions and also effective for the treatment of chronic rheumatoid arthritis, leads to the reduction of expected pharmacological activities.

In order to potentiate the synergic effects of the mixed ingredients rather than a single component, in particular, this invention is designed to extract three kinds of combined medicinal plants (Clematis Radix, Trichosabthes root and Prunella Herba) collectively rather than separate extraction. Hence, the most remarkable efficacy can be manifested by a blending ratio specified above.

The combined medicinal plants in said blending ratio are diluted with water or alcoholic solution and extracted under reflux for 2 to 5 hours. Hence, 10–15 volumes of water or alcoholic solution is preferable to the weight of said combined medicinal plants. Then, the resulting mixture is filtrated for summing up afterwards.

The residue is once again diluted with 7–12 volumes of water or alcoholic solution to the weight of combined medicinal plants. The residue is diluted with heating for 2 to 5 hours and filtrated. The filtrate is mixed with previously prepared solution to enhance the extraction efficiency. Hence, if a small amount of water is used, stirring is poor so extraction efficiency is lowered by the lower solubility of extract. In case of using an excess of water, however, a larger amount of solvent saturated with lower alcohol in water is required in the next purification step, therefore which is uneconomical and difficult in handling.

This invention adopts a series of extraction steps, i.e., first and second extraction, the reason of which can be found in the following: When extraction is on a large scale, significant losses are anticipated due to high contents of water in medicinal plants, in spite of effective filtration. So a second extraction is responsible for preventing the reduced extraction efficiency rather than the first extraction only. Further, as a result of investigating the extraction efficiency in each step, it is revealed that about 80–90% of extracts may be yielded through two extractions to the total amount. It is judged that more than three steps of extraction is uneconomical.

The resulting solution, extracted with water for two steps, is filtrated.

The filtrate is further purified to remove some impurities such as polar organic acids, proteins, polysaccharides and fatty acids. According to this invention, the purification process is conducted in such a manner that the remaining solution is extracted with the same amount of lower alcohol saturated with water by three or four times, to obtain the solvent fraction. Hence, butanol or propyl alcohol is used as lower alcohol; if the amount of water-saturated lower alcohol is less than that of the remaining solution, a higher concentration of impurities (e.g., polysaccharides and proteins) having relatively strong polarity causes lower concentration of active ingredients in the extracts.

After separating the layers, the obtained fractions extracted with alcohol solvent are concentrated under reduced pressure at 60–70° C. to remove lower alcohol solvent in the sample. Then, the obtained extract is further concentrated under constant boiling with 50–100 volumes of water to the total extract amount and followed with another same amount of water for homogeneous suspension. The reason why the residue is concentrated under constant boiling with water during concentration and drying is to control the contents of remaining lower alcohol so as to use the extracting solution as pharmaceutical raw materials.

The extract, so obtained, is lyophilized to give a powder. Compared to some aqueous extracts obtained by the method of hot water extraction from each of Clematis Radix, Trichosabthes root and Prunella Herba, as listed in the conventional herbal books such as Dong-Eui-bo-gam, Bonchogangmok and Hyangyak Gibsungbang, this extract has significant pharmacological activities, such as analgesic & anti-inflammatory effects, anti-coagulant actions in platelet and whole blood, inhibitory actions on enzymes associated with degradation of joint tissue, inflammation-inducing enzyme activity and regulation of abnormally proliferated immunocytes and also to improve, scavenging actions on toxic active oxygen species, curation of chronic rheumatoid arthritis. Thus said plant extract may be effectively used for the treatment of chronic rheumatoid arthritis.

As a result of analyzing the biologically effective ingredients extracted from the combined medicinal plants containing Clematis Radix, Trichosabthes root and Prunella Herba by HPLC, it is revealed that rosmarinic acid is contained in the extract. Further, when the extract is hydrolyzed, sufficient amounts of oleanolic acid are present as sapogenin, a sugar-free form of saponins.

Several researchers have reported that oleanolic acid has a remarkable anti-inflammatory and analgesic effects, while being effective for chronic rheumatoid arthritis induced by Mycobacterium butyricum [1. journal of Pharm. Phamacol., 44(5), pp456–458(1992); 2. Chung-Kuo-Li-Hsueh-Pao, 10(4), pp381–384(1989)].

Further, rosmarinic acid has been found to inhibit the biosynthesis of prostacyclin generated in the metabolism of arachidonic acid.

It has been also reported that the extract has an anti-inflammatory action since it scavenges the active oxygen generated by polymorphonuclear [I. Biochem. Pharmac., 29, pp533–538(1980); 2. Agents Actions, 17, pp375–376 (1985)].

Rosmarinic acid and oleanolic acid are the active ingredients of combined extract preparation obtained from this invention. The efficacy is far more potent in the combined preparation of substance than those of substance independently, because of parallelism with the synergic effect of drug. Adequate efficacy may be demonstrated with small amounts of the extract. Further, in addition to rosmarinic acid and oleanolic acid as active ingredients of the combined preparation obtained from this invention, other different ingredients cannot be ruled out in this invention.

Meantime, according to this invention, it is revealed that the most preferable weight ratios of both rosmarinic acid and oleanolic acid in the extract are 0.3–0.6% (w/w) and 3.0–7.0% (w/w), respectively, in order that the extract of this invention may demonstrate generally significant pharmacological activities with remarkable synergic effects, such as analgesic & anti-inflammatory effects, anti-coagulant actions in platelet and whole blood, inhibitory actions on enzymes associated with degradation of joint tissue, inflammation-inducing enzyme activity and regulation of abnormally proliferated immunocytes and also to improve scavenging actions on toxic active oxygen species, and curation of chronic rheumatoid arthritis.

In other words, only when the extracts are extracted and purified from the combined plants in a certain ratio, the extracts shall contain the index constituents, oleanolic acid and rosmarinic acid, above specified level, giving the effect on the chronic rheumatoid arthritis.

Meanwhile, when the combined plant preparation is first extracted with alcoholic solution and fractionated with water saturated butanol, certain concentrations of both rosmarinic acid and oleanolic acid, index constituents, are also contained in the extract and there is no difference in therapeutic effects compared with the process of manufacturing the extract fractionated with butanol after hot water extraction.

Based on the general manufacturing method, the powdered extract of this invention is formulated in various dosage forms such as tablets, soft capsules, gels, creams, and injectables. With mixtures of base material, microcrystalline cellulose and magnesium stearate, and the combined plant extract of this invention in a ratio of 2:1, the tablets may be manufactured effective in chronic rheumatoid arthritis.

In particular, while the plant composition of this invention was administered to the human, the toxic side effect is far less than other chemically synthesized drugs. As a matter of fact, several toxicological tests reveal that the combined extract of this invention is not toxic to the human body.

Unlike some conventional extracts obtained from hot water extraction, as mentioned above, the plant extract of this invention, prepared by mixing three kinds of medicinal plants (e.g., Clematidis Radix, Trichosabthes root and Prunellae Herba) in a certain ratio, has superior pharmacological activities. Further, the plant extract containing 3 kinds of medicinal plants has been formulated in a dosage form of medicinal decoction only is also available in various administration-convenient dosage forms such as tablets, injectables, and ointments, gels, creams.

DETAILED DESCRIPTION OF THE INVENTION

Figure 1:
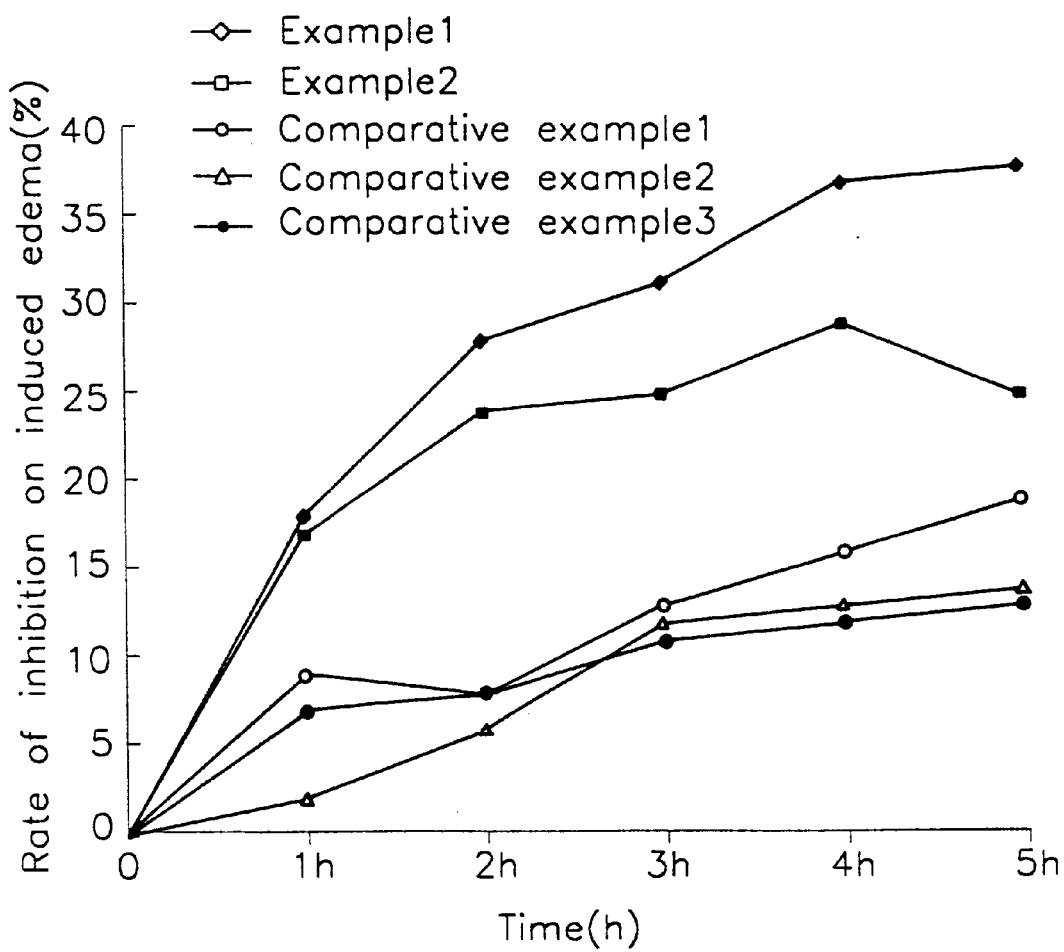
FIG. 1 shows the inhibitory activity of the plant extracts on edema induced by carrageenan in rats with the lapse of time. Each extract was prepared by example 1–2 of this invention and comparative example 1–3.

This invention is explained in more details with reference to the following examples, which does not necessarily limit this this invention.

Example 1

250 g of well air dried Clematis Radix where debris were removed by tap water and allowed to be dried in the shade overnight, 500 g of finely chopped Trichosabthes root in a size of 1.0–2.0 cm and 250 g of Prunella Herba from the flower collected during late summer are well mixed and stirred with the addition of 15 L water. The mixture was extracted under reflux for 3 hours with boiling and mixed with previously prepared solution (20 L). The mixing solution was extracted with a same volume of n-butanol saturated water three times. The n-butanol layer were gathered and concentrated under reduced pressure at 60–70° C. until the medicinal plant extract was dried. After evaporating a majority of n-butanol and water, the extract was further concentrated with the addition of 1.5 L of water under constant boiling and repeated the procedure two times. Finally, the extract was well suspended in a same amount of distilled water and lyophilized to give 24 g of powdered extract. According to chemical analysis of powered extract by gas chromatography and high performance liquid chromatography, the residual n-butanol was 150 ppm, while the contents of oleanolic acid and rosmarinic acid were 6.11% and 0.45%, respectively.

Example 2

Each 330 g of Clematis Radix, Trichosabthes root and Prunella Herba, purchased in the local market, was mixed well and stirred with the addition of 10 L water. The reacting mixture was extracted under reflux for about 5 hours. After collecting the remaining solution, about 10 L water was further added to the residue, which was extracted by refluxing for about 3 hours and then this remaining solution was brought up (15 L). The mixing solution was extracted three times with a same volume of n-butanol saturated with water. All n-butanol layers were concentrated under reduced pressure at 60–70° C. Finally, the extract was well suspended in 2 L of distilled water and lyophilized to give 35 g of powdered extract. According to chemical analysis of powder extract by gas chromatography and high performance liquid chromatography, the residual n-butanol was 128 ppm, while the contents of oleanolic acid and rosmarinic acid were 5.05% and 0.55%, respectively.

Comparative Example 1

By the method of standard decoction formulation, Clematidis Radix, purchased in the local market, was extracted with water, filtered and lyophilized to give a powdered extract. The resulted powdered extract was subjected to HPLC and according to its chemical composition, the contents of oleanolic acid and rosmarinic acid were less than 0.23% and 0.03%, respectively.

Comparative Example 2

By the method of standard decoction formulation, Trichosanthes root, purchased in the local market, was extracted with water, filtered and lyophilized to give a powdered extract. The resulted powdered extract was subjected to HPLC and according to its chemical composition, the contents of oleanolic acid and rosmarinic acid were less than 0.01% and 0.01%, respectively.

Comparative Example 3

By the method of standard decoction formulation, Prunella Herba, purchased in the local market, was extracted with water, filtered and lyophilized to give a powdered extract. The resulted powdered extract was subjected to HPLC and according to its chemical composition, the contents of oleanolic acid and rosmarinic acid were less than 0.01% and 0.75%, respectively.

Reference 1

Clematis Radix, Trichosabthes root and Prunella Herba were mixed in a weight ratio of 1:2:1 and according to the same procedure described above, hot water extraction and butanol fractionation were performed three times, respectively. The amount of extract obtained from each step to the total yield was expressed by percent and the results were presented in the following table 1.

TABLE 1

| Yields of hot water extract and butanol fraction in each step | | | |
|---|---|---|---|
| Classification | 1st | 2nd | 3rd |
| Hot water extract | 65% | 25% | 10% |
| Butanol fraction | 52% | 28% | 20% |

From the above table 1, the progression to the third step is uneconomical in that the 80 to 90% of the total extracts was obtained from said two steps.

Reference 2

According to this invention, Clematis Radix, Trichosabthes root and Prunella Herba were mixed in a weight ratio of 1:2:1. Then, a hot water extraction and butanol fractionation were performed and then oleanolic acid and rosmarinic acid, index constituents of each test sample, was purified. As a result, it was noted that two index constituents were transferred to butanol fraction, as shown in table 2.

TABLE 2

| Analysis of index constituents on transfer rate. | | | |
|---|---|---|---|
| | Dried herbal medicine (100 g) | Hot water extract (Yield: 19.6%) | Fractionated butanol (Yield: 3.2%) | Transfer rate |
| Oleanolic acid | — | 0.75% | 4.08% | 88.8% |
| Rosmarinic acid | — | 0.094% | 0.51% | 88.6% |

Reference 3

Index compositions of two combined plant extracts in powder form were compared; One was prepared by this invention using three kinds of domestic medicinal plants containing Clematis Radix and Trichosabthes root collected at autumn and Prunella Herba collected at late summer and the other was prepared by the same method as in this invention using three kinds of Chinese medicinal plants. Two combined plant extracts were subjected to HPLC for the analyzing the contents of oleanolic acid and rosmarinic acid, as shown in table 3.

TABLE 3

Comparison of index constituents from
combined preparations prepared by domestic and
Chinese medicinal plants

|  | Oleanolic acid | Rosmairinic acid |
|---|---|---|
| Combined preparations from domestic medicinal plant | 4.76% | 0.48% |
| Combined preparations from Chinese medicinal plant | 5.28% | 0.39% |

Reference 4

Toxicology Test

The dried plant extract in powder form prepared from EXAMPLE I was orally administered to white SD (Spraque-Dawley) rats at a dose of 2 g/kg.

No death was observed in animals for two weeks. In comparison with the control, there was no abnormality in other anatomical findings.

Therefore, the dried extract in powder form prepared from EXAMPLE 1 is deemed as an extremely safe substance.

Test 1

To investigate the analgesic effects of various extracts prepared by said example 1–2 and comparative example 1–3, writhing test induced by acetic acid was conducted as presented in the following table 4.

Experimental Method:

The plant extracts, prepared by said example 1–2 and comparative example 1–3, were orally administered to ICR (Institute of Cancer Research) rats at doses of 200 mg, 400 mg per kg of body weight.

One hour after administration, 0.6% acetic acid was intraperitoneally injected to rats at a dose of 0.1 ml per 10 g of body weight and 10 minutes after administration, writhing frequency of each rat as a pain threshold was observed for 10 minutes.

TABLE 4

|  | Dose of herbal medicine extract (mg/kg) | Avg. writhing frequency | rate of inhibition (%) |
|---|---|---|---|
| Control | — | 20 | — |
| Example 1 | 200 | 12 | 40 |
|  | 400 | 9 | 55 |
| Example 2 | 200 | 13 | 35 |
|  | 400 | 10 | 50 |
| Comparative example 1 | 200 | 15 | 25 |
|  | 400 | 14 | 30 |
| Comparative example 2 | 200 | 13 | 35 |
|  | 400 | 11 | 45 |
| Comparative example 3 | 200 | 13 | 35 |
|  | 400 | 10 | 50 |

From said table 4, it is revealed that the extract prepared by this invention has superior analgesic effects from reduced writhing frequencies.

Test 2

The inhibitory activity of plant extracts, prepared by said example 1–2 and comparative example 1–3, on acute inflammation was investigated in rats inflamed by carrageenan. In comparison with the control, the inhibitory rate of edema in the rats hind paw was expressed as percent and its results are presented in the attached FIG. 1.

Experimental Method:

The plant extracts, prepared by example 1–2 and comparative example 1–3, was orally administered to white SD (Spraque-Dawley) rats. One hour after drug administration, 0.1 ml of 1% carrageenan was intradermally injected to the left hind paw of rats and edema at that site was observed at 1 hour interval for 5 hours.

As noted in the attached FIG. 1, it is revealed that the plant extracts prepared by example 1 and 2 of this invention significantly inhibited the carrageenan-induced inflammation.

Test 3

Figure 2:
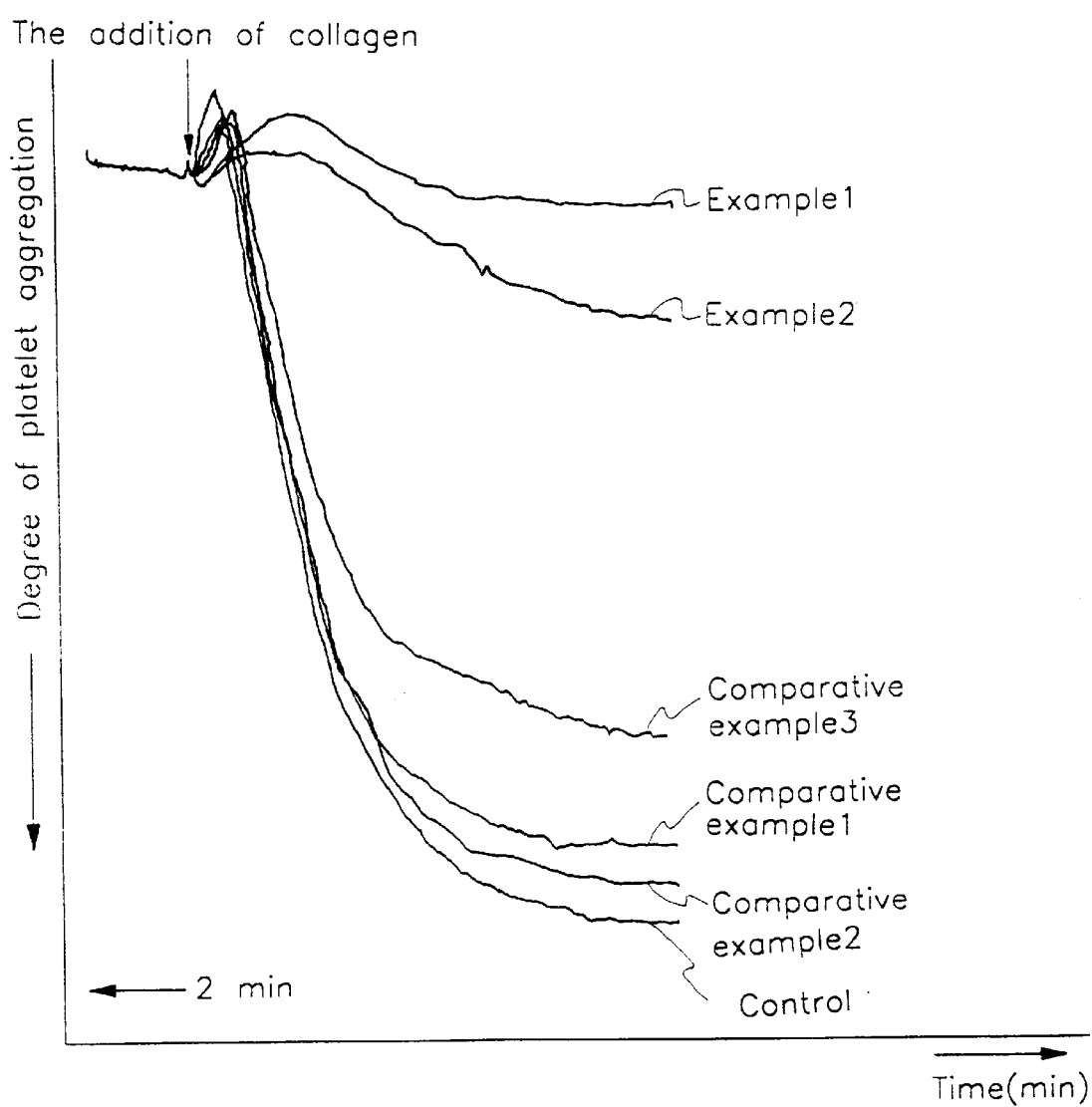
FIG. 2 shows the anti-coagulant activity of the extracts on platelet aggregation induced by collagen with the lapse of time. The extracts are the same in FIG. 1.

The anti-coagulant activity of plant extracts, prepared by said example 1–2 and comparative example 1–3, on platelet was investigated in rabbits induced by collagen and its results are presented in the attached FIG. 2.

Experimental Method:

PRP (platelet rich plasma) was prepared from the blood sample of rabbits and the number of platelet in blood was adjusted at $2 \times 10^8$/ml. Then the plant extract prepared by example 1–2 and comparative example 1–3 were added to the blood and adjusted on a cuvette of aggregometer at 37° C. for 2 minutes. With the addition of collagen thereafter, the inhibitory rate of platelet aggregation was measured.

As noted in the attached FIG. 2, there was no increase in platelet aggregation with the lapse of time.

Test 4

Figure 3:
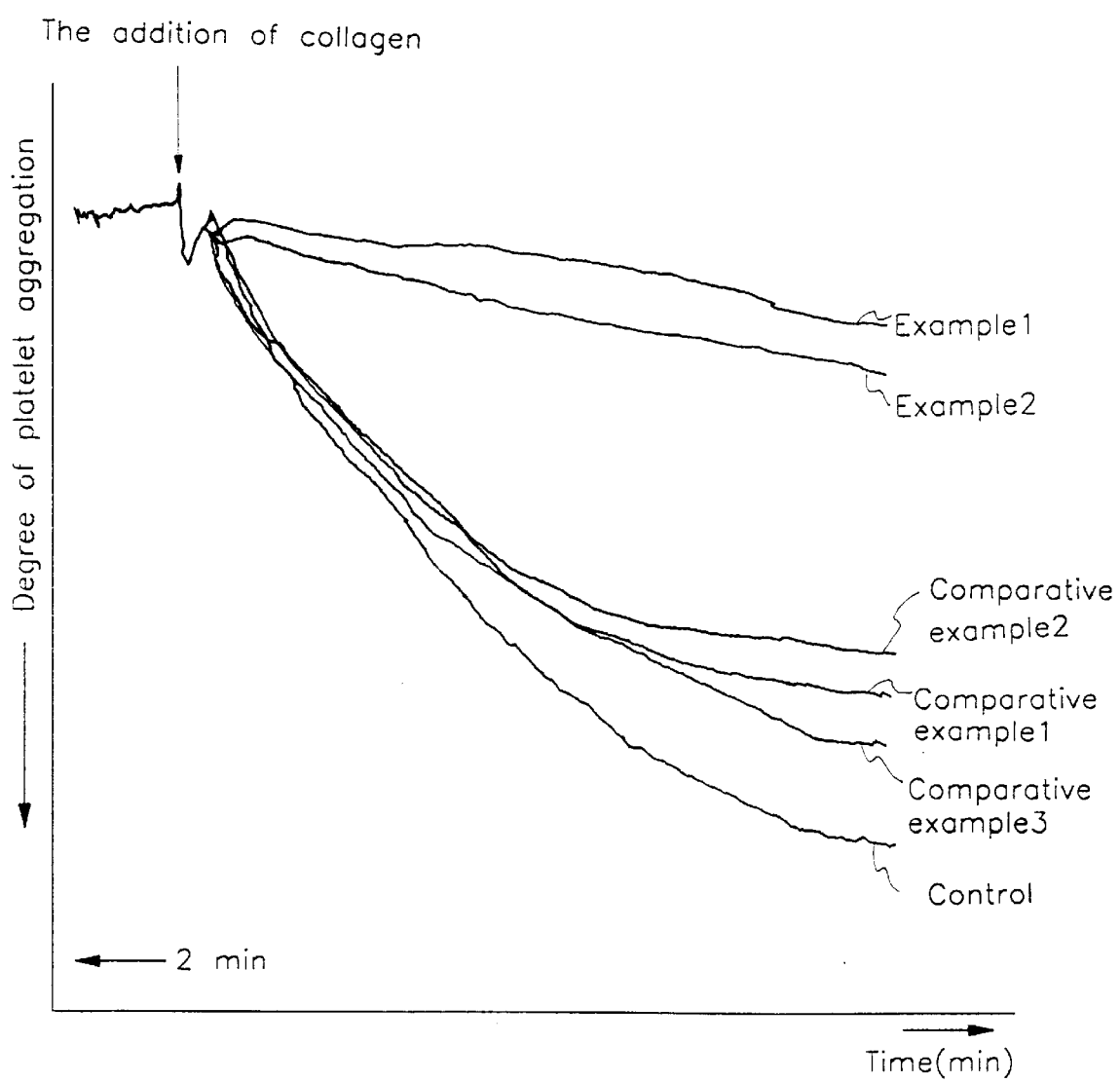
FIG. 3 shows the anti-coagulant activity of the extracts on whole blood aggregation induced by collagen with the lapse of time. The extracts are the same in FIG. 1.

The anti-coagulant activity of the extracts, prepared by said example 1–2 and comparative example 1–3, on the whole blood was investigated in rabbits induced by collagen and its results are presented in the attached FIG. 3.

Experimental Method:

A same amount of saline solution was added to whole blood and mixed well prior to use in this experiment. The sample extracts, so obtained from example 1–2 and comparative example 1–3, were added to previously cultured blood at 37° C. on the cuvette of aggregometer and cultured for another 2 minutes. Hereafter, the blood coagulation with the addition of collagen was measured by a aggregometer. As shown in the attached FIG. 3, it is revealed that there was no increase in whole blood aggregation, when the extract of this invention was added.

Test 5

The inhibitory activity of the extracts, prepared by said example 1–2 and comparative example 1–3 on hyaluronidase, an enzyme associated with degradation of joint tissue, were investigated and its results are presented in the following table 5.

Experimental Method:

Hyaluronidase was cultured in the presence of acetate buffer solution at 37° C. for 20 minutes and activated. Then the extracts prepared by example 1–2 and comparative example 1–3 and potassium hyaluronate as a substrate were added to the cultures and cultured for about 40 minutes. After terminating the reaction with NaOH, potassium borate was added to the cultures and heated at 100° C. The absorptivity was measured by the development of DMBA (Dimethylbenzanthracene) and the rate of inhibition was calculated in comparison with control.

TABLE 5

|  | Test conc. (mg/ml) | rate of Inhibition |
|---|---|---|
| EXAMPLE 1 | 1 | 80 |
| EXAMPLE 2 | 1 | 80 |
| COMPARATIVE EXAMPLE 1 | 1 | 10 |
| COMPARATIVE EXAMPLE 2 | 1 | 20 |
| COMPARATIVE EXAMPLE 3 | 1 | 70 |

As shown in table 5 as above, the combined plant extracts prepared by this invention significantly inhibited the activation of the enzyme associated with degradation of joint tissue.

Test 6

Figure 4:
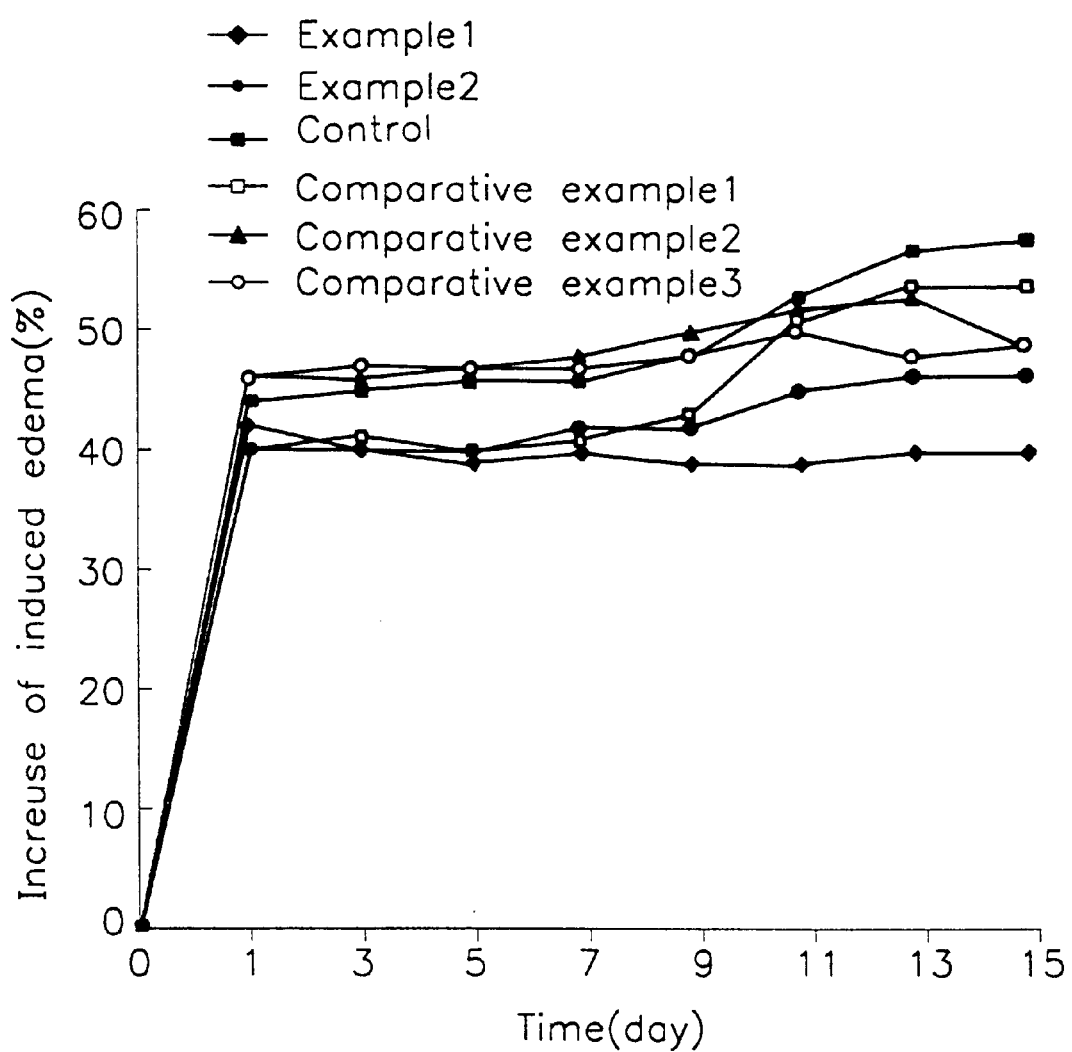
FIG. 4 shows the inhibitory activity of the extracts on edema induced by Mycobacterium butyricum with the lapse of time. The extracts are the same in FIG. 1.

The anti-inflammatory activity of the extracts, prepared by said example 1–2 and comparative example 1–3, on chronic rheumatoid arthritis was investigated in rats induced by Mycobacterium butyricum and its results are presented in the attached FIG. 4.

Experimental Method:

To induce chronic edema, Mycobacterium butyricum suspended in mineral oil and treated with heat was injected to the right hind paw of white rats at each dose of 0.05 ml. Then the extracts, prepared by said example 1–2 and comparative example 1–3, was administered to the rats for 15 days so as to measure the degree of edema. Each of the extracts were orally administered to the rats once daily for 16 days.

Figure 5:
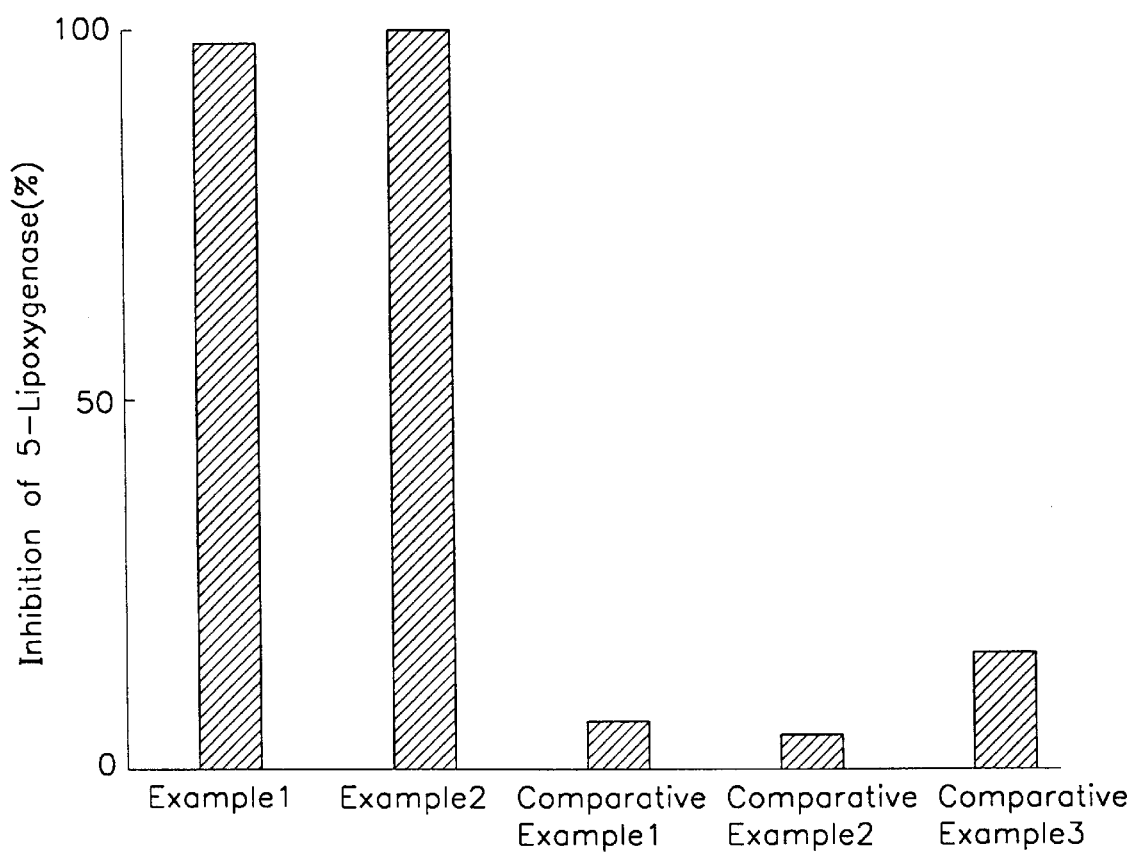
FIG. 5 shows the inhibitory activity of the extracts on 5-Lipoxygenase. The extracts are the same in FIG. 1.

As shown in the attached FIG. 5, the combined plant extracts prepared by this invention significantly inhibited the edema.

Test 7

The inhibitory activity of the extracts, prepared by said example 1–2 and comparative 1–3 on 5-Lipoxygenase was compared by the inhibition rate of Leukotriene B4 (LTB4) induced by arachidonic acid and calcium ionophore (A23187) and its results are presented in the attached FIG. 5.

Experimental Method:

The extracts, prepared by said example 1–2 and comparative example 1–3, were added to RBL-1 (Rat Blood Leukemia-1) cells adjusted at 37° C. and reacted for 5 minutes. Then the reacting mixture was treated with 20 µg/ml arachidonic acid with the concurrent addition of 1 µg/ml A23187 at 15 minutes so as to induce the generation of LTB4. The generated LTB4 was extracted with ethylacetate and was subjected to HPLC.

As shown in the attached FIG. 5, the combined plant extracts prepared by this invention significantly inhibited 5-lipoxygenase activitity than those prepared by comparative example 1–3.

Test 8

Figure 6:
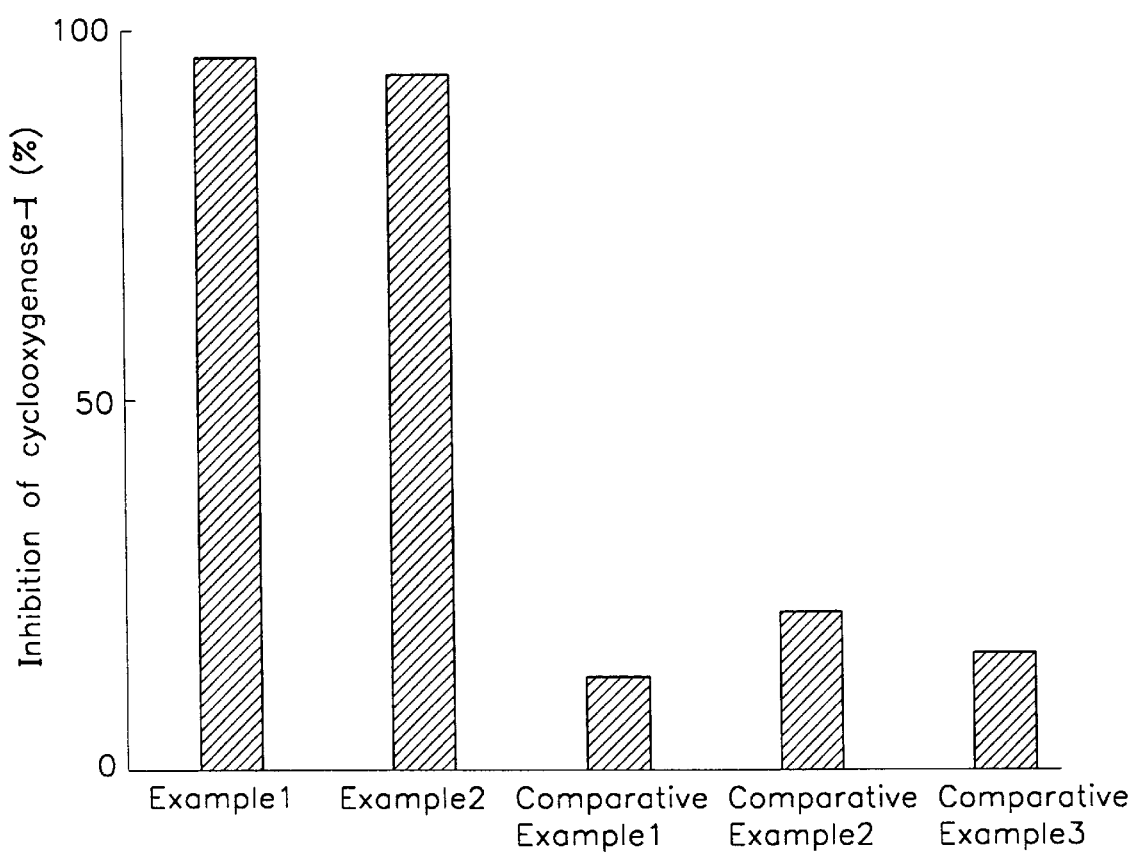
FIG. 6 shows the inhibitory activity of the extracts on Cyclooxygenase-I. The extracts are the same in FIG. 1.

The inhibitory activity of the extracts, prepared by said example 1–2 and comparative example 1–3 on Cyclooxygenase-I induced by arachidonic acid and its results are presented in the attached FIG. 6.

Experimental Method:

The extracts, prepared by said example 1–2 and comparative example 1–3, were added to Cyclooxygenase-I adjusted at 37° C. After reaction with 100 mM arachidonic acid for 2 minutes, trichloroacetic acid (TCA) was added to the reacting mixture for terminating the reaction and absorbance was measured at 530 nm.

As shown in the attached FIG. 6, the combined plant extracts prepared by this invention significantly inhibited Cyclooxygenase-I activitity than those prepared by comparative example 1–3.

Test 9

Figure 7:
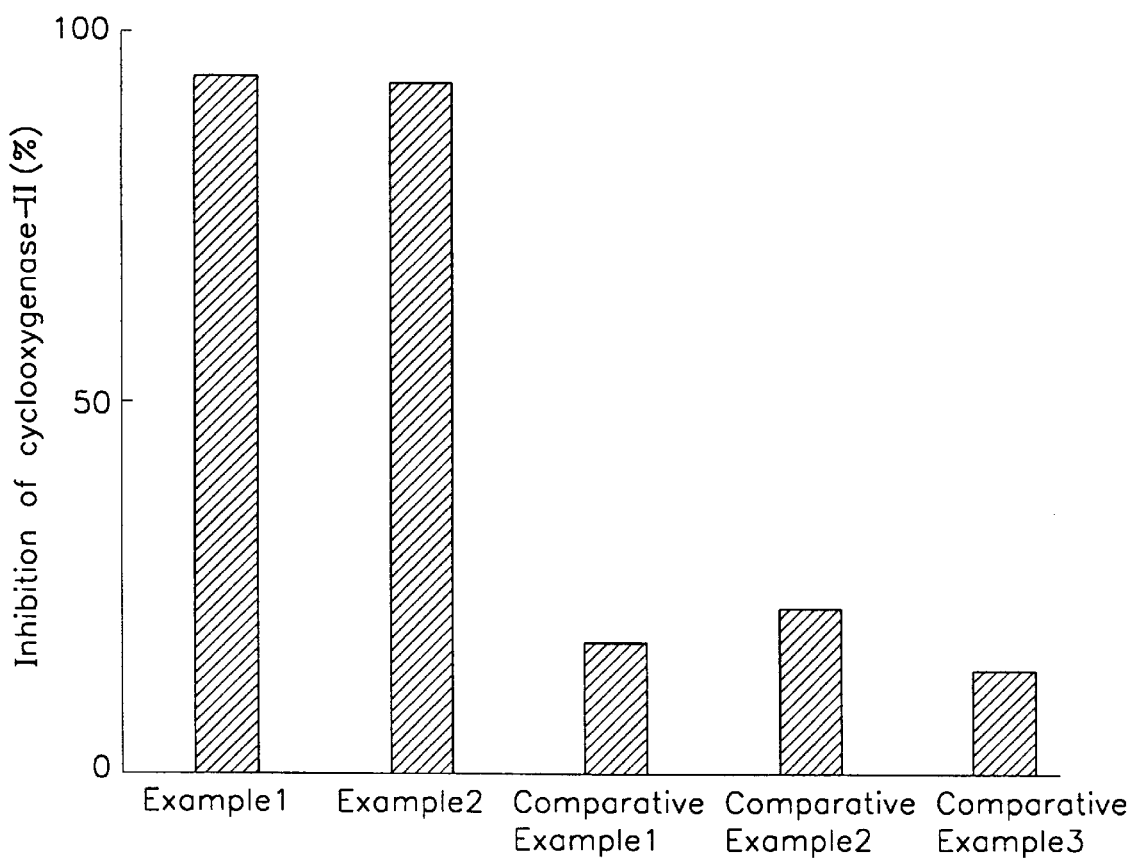
FIG. 7 shows the inhibitory activity of the extracts on Cyclooxygenase-II. The extracts are the same in FIG. 1.

The inhibitory activity of the extracts, prepared by said example 1–2 and 5 comparative example 1–3, on Cyclooxygenase-11 induced by arachidonic acid and its results are presented in the attached FIG. 7.

Experimental Method:

Cyclooxygenase-II was placed at a test tube adjusted at 27° C. with the concurrent addition of the extracts, prepared by said example 1–2 and comparative example 1–3. After reaction with 500 mM arachidonic acid for 90 seconds, trichloroacetic acid (TCA) was added to the reaction mixture for terminating the reaction and absorbance was measured at 532 nm.

As shown in the attached FIG. 7, it is noted that the combined plant extracts prepared by this invention significantly inhibited Cyclooxygenase-II activity than those prepared by comparative example 1–3.

Test 10

Figure 8:
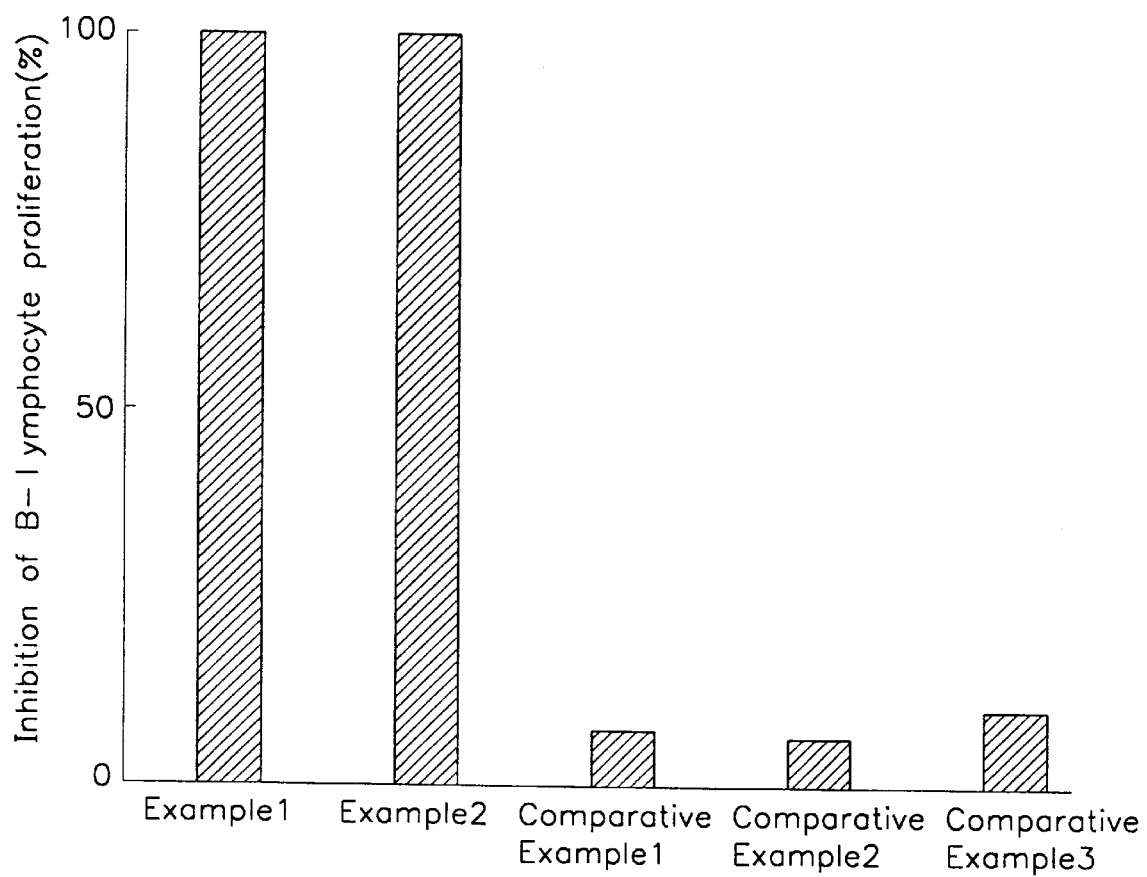
FIG. 8 shows the inhibitory activity of the extracts on B-lymphocyte. The extracts are the same in FIG. 1.

The inhibitory activity of the extracts, prepared by said example 1–2 and comparative example 1–3 on the proliferation of B-lymphocyte induced by Lipopolysaccharide (LPS) and its results are presented in the attached FIG. 8.

Experimental Method:

Cultures were set up with $10^6$ T-lymphocyte/ml of medium at 37° C. The extracts prepared by said example 1–2 and comparative example 1–3 were added to the cultures, which were treated with 10 µg/ml of LPS for 24 hours. With the addition of 2 mCi Thymidine-$^3$H expressed by tritium as radioactivity for 48 hours, cultures were quantitized on Liquid Scincillation Counter (LSC).

As shown in the attached FIG. 8, it is noted that the combined plant extracts prepared by this invention significantly inhibited the proliferation of B-lymphocyte than those prepared by comparative example 1–3.

Test 11

Figure 9:
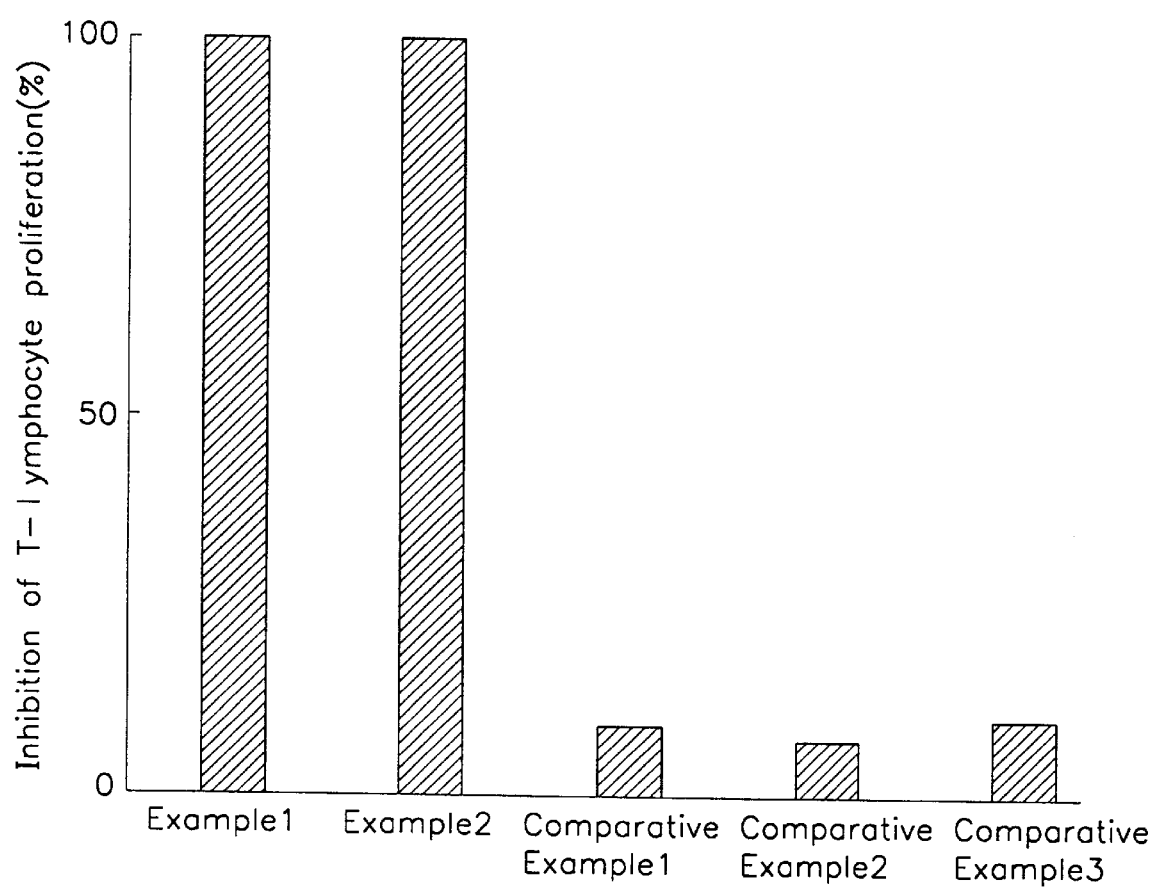
FIG. 9 shows the inhibitory activity of the extracts on T-lymphocyte. The extracts are the same in FIG. 1.

The inhibitory activity of the extracts, prepared by said example 1–2 and comparative example 1–3 on the proliferation of T-lymphocyte induced by Concanavalin-A (Con-A) and its results are presented in the attached FIG. 9.

Experimental Method:

Cultures were set up with $5\times10^6$ T-lymphocyte/ml of medium at 37° C. The extracts prepared by said example 1–2 and comparative example 1–3 were added to the cultures, which were treated with 3 µg/ml of Concanavalin-A for 24 hours. With the addition of 2 mCi Thymidine-$^3$H expressed by tritium as radioactivity for 48 hours, cultures were purified on Liquid Scincillation Counter (LSC).

As shown in the attached FIG. 9, it is noted that the combined plant extracts prepared by this invention significantly inhibited the proliferation of T-lymphocyte than those prepared by comparative example 1–3.

Test 12

Figure 10:
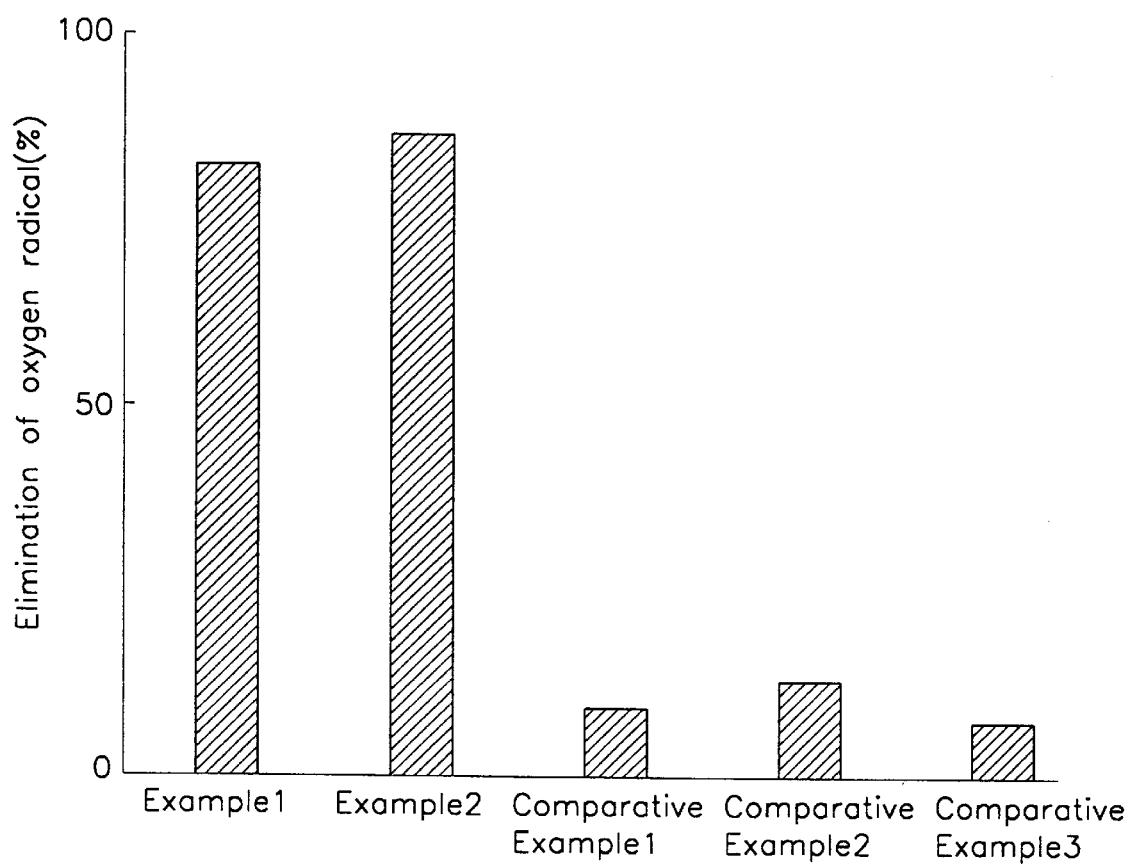
FIG. 10 shows the scavenging activity of the extracts on superoxide radical. The extracts are the same in FIG. 1.

The scavenging activity of the extracts, prepared by said example 1–2 and comparative example 1–3, were assessed on elimination of superoxide radicals generated from xanthine-xanthine oxidase and its results are presented in the attached FIG. 10.

Experimental Method:

Cytochrome-c (Cyt-c) and extracts, prepared by example 1–2 and comparative example 1–3, were added to xanthine oxidase adjusted at 37° C. so as to induce the generation of oxygen radicals by xanthine. The changes in color along with oxidation of Cytochrome-c (Cyt-c) was measured by spectrophotometer at 540 nm and seavenging rate of oxygen radicals was also measured as slope.

As shown in the attached FIG. 10, it is noted that the combined plant extracts prepared by this invention significantly scavenged active oxygen than comparative example 1–3.

Manufacture 1

The following chemical composition was employed for the manufacture of oral tablets using the powdered extract prepared by said example 1.

| Chemical composition | |
|---|---|
| Powdered extract of example 1 | 100 mg |
| Hard anhydroud silicate | 10 mg |
| Magnesium stearate | 5 mg |
| Microcrystalline cellulose | 190 mg |
| Sodium starch glycolate | 60 mg |
| Anhydrous calcium monohydrogen phosphate | 135 mg |

Manufacture 2

The following chemical composition was employed for the manufacture of oral tablets using the powdered extract prepared by said example 1.

| Chemical composition | |
|---|---|
| Powdered extract of example 1 | 200 mg |
| Hard anhydrous silicate | 20 mg |
| Magnesium stearate | 7 mg |
| Microcrystalline cellulose | 230 mg |
| Sodium starch glycolate | 80 mg |
| Anhydrous Calcium monohydrogen phosphate | 163 mg |

Manufacture 3

The following chemical composition was employed for the manufacture of ointments using the powdered extract prepared by said example 1.

| Chemical composition | |
|---|---|
| Powdered extract of example 1 | 5 g |
| Fluid paraffin | 10 g |
| sperm wax | 9 g |
| Ethanol | 8 g |
| Sorbitan monooleate | 2 g |
| Polysophbate | 4 g |
| p-hydroxybenzoic acid propyl ester | 0.05 g |
| p-hydroxybenzoic acid methyl ester | 0.1 g |
| Conc. glycerin | 10 g |
| Purified water | q.s. |

Manufacture 4

The following chemical composition was employed for the manufacture of injectables using the powdered extract prepared by said example 1.

| Chemical composition | |
|---|---|
| Injectable ampule: | |
| Powdered extract of example 1 | 100 mg |
| Mannitol | 180 mg |
| Corresponding solvent ampoule: | |
| $Na_2HPO_4 \cdot 12H_2O$ | 26 mg |
| Injectable water | 2974 mg |

Several dosage forms (e.g., tablets, ointments and injectables) prepared by said manufacture 1–4 related to combined herbal preparations using Clematis Radix, Trichosabthes root and Prunella Herba according to this invention.

Said prepreparations contain concentrations of oleanolic acid and rosmarinic acid as index constituents, thus being effectively used for anti-inflammatory agent with analgesic effects, chronic rheumatoid arthritis drug and agent for improving peripheral blood circulation.

What is claimed is:

1. A combined medicinal plant composition comprising the extract from a mixture of plants, wherein said mixture of plants comprises Clematis Radix, Trichosabthes root and Prunella Herba.

2. The combined medicinal plant composition of claim 1, wherein said mixture comprises Clematis Radix, Trichosabthes root and Prunella Herba in a weight ratio of 1:0.5–2:0.5–1.5.

3. The combined medicinal plant composition of claim 1, wherein said extract comprises rosmarinic acid and oleanolic acid.

4. The combined medicinal plant composition of claim 3, wherein said rosmarinic acid is present in said extract in an amount from 0.3 to 0.6 percent by weight with respect to the total weight of the extract.

5. The combined medicinal plant composition of claim 3, wherein said oleanolic acid is present in said extract in an amount from 3.0 to 7.0 percent by weight with respect to the total weight of the extract.

6. A process for manufacturing a combined herbal extract preparation comprising:

(1) obtaining an extract from a mixture of Clematis Radix, Trichosanthes root and Prunella Herba in a weight ratio of 1:0.5–2:0.5–1.5 with water or alcoholic solution;

(2) partitioning the extract with water-saturated alcohol to produce an alcohol layer, wherein the alcohol is selected from the group consisting of n-butanol and propyl alcohol;

(3) concentrating under reduced pressure the resulting alcohol layer; and (4) thereafter forming a powdered extract by boiling the concentrated alcohol layer with water, and and thereafter lyophilizing the boiled layer.

7. A process for manufacturing combined herbal preparations of claim 6, wherein said extraction step comprises extracting a mixture of medicinal plants under reflux with 10 to 15 volumes of water or alcoholic solution to the weight of said mixture and following filtration, heating the residue with 7 to 12 volumes of water or alcoholic solution to the weight of said mixture and followed with another filtration, and adding the filtration to previously prepared extract solution.

8. A process for manufacturing combined herbal preparations of claim 6, wherein said concentration under reduced pressure is conducted at 60 to 70° C.

9. The process for manufacturing a combined herbal preparation of claim 6, wherein said boiling is conducted at least twice with 50 to 100 volumes of water with respect to the total weight of the extract.

10. An anti-inflammatory agent with analgesic effects comprising as an active ingredient the extract of claim 1.

11. A drug for treatment of chronic rheumatoid arthritis comprising as an active ingredient the extract of claim 1.

12. A drug for improving peripheral blood circulation, comprising as an active ingredient the extract of claim 1.

13. The process of claim 6 wherein said alcohol is n-butanol.

* * * * *